(12) United States Patent
Maroney et al.

(10) Patent No.: US 7,450,224 B2
(45) Date of Patent: Nov. 11, 2008

(54) DETERMINATION OF THE BOUNDARIES BETWEEN FRACTIONS AND EXTRACTION OF SELECTED FRACTIONS IN A FRACTIONATED SAMPLE

(75) Inventors: William John Maroney, Radcliffe (GB); Simon Michael Sheard, Stockport (GB); David Charles Lee, Altrincham (GB)

(73) Assignee: RTS Life Science Ltd., Iram, Manchester (GB)

( * ) Notice: Subject to any disclaimer, the term of this patent is extended or adjusted under 35 U.S.C. 154(b) by 0 days.

(21) Appl. No.: 12/013,966

(22) Filed: Jan. 14, 2008

(65) Prior Publication Data

US 2008/0111988 A1      May 15, 2008

Related U.S. Application Data

(63) Continuation of application No. 11/181,566, filed on Jul. 13, 2005, now abandoned.

(30) Foreign Application Priority Data

Oct. 8, 2004   (GB)  ................................. 0422358.2

(51) Int. Cl.
*G01N 33/48*   (2006.01)

(52) U.S. Cl. ........................................ 356/39; 382/134

(58) Field of Classification Search ................... 356/39; 382/133, 134
See application file for complete search history.

(56) References Cited

U.S. PATENT DOCUMENTS

| | | | | |
|---|---|---|---|---|
| 4,927,545 A | * | 5/1990 | Roginski | ..................... 210/745 |
| 5,308,506 A | * | 5/1994 | McEwen et al. | ............ 210/745 |
| 5,745,227 A | * | 4/1998 | Dufresne et al. | .............. 356/39 |
| 5,763,265 A | | 6/1998 | Itsuzaki et al. | |
| 6,743,398 B2 | * | 6/2004 | Itoh | ........................... 422/73 |
| 6,770,883 B2 | * | 8/2004 | Mc Neal et al. | .......... 250/341.1 |

FOREIGN PATENT DOCUMENTS

| | | |
|---|---|---|
| DE | 102 21 285 A1 | 8/2003 |
| JP | 09133687 A | 5/1997 |
| JP | 11248853 A | 9/1999 |
| JP | 2001165752 A | 6/2001 |

* cited by examiner

*Primary Examiner*—Roy M Punnoose
(74) *Attorney, Agent, or Firm*—Amster, Rothstein & Ebenstein LLP

(57) ABSTRACT

An apparatus and method are provided for determining boundaries between fractions in a fractionated sample. The method includes the steps of providing the fractionated sample in a receptacle, the receptacle having a transparent window, positioning the receptacle in a known position relative to datum means, capturing an image of the receptacle and datum means, and processing the image to determine the position of boundaries between the fractions in the sample relative to the datum means. An apparatus and method for extracting a selected fraction of a fractionated sample are also disclosed.

40 Claims, 2 Drawing Sheets

DETERMINATION OF THE BOUNDARIES BETWEEN FRACTIONS AND EXTRACTION OF SELECTED FRACTIONS IN A FRACTIONATED SAMPLE

CROSS-REFERENCE TO RELATED APPLICATIONS

This application is a continuation of application Ser. No. 11/181,566, filed Jul. 13, 2005, now abandoned the contents of which are incorporated herein by reference.

BACKGROUND OF THE INVENTION

The present invention relates to a method and apparatus for automatically determining the boundaries between fractions in a fractionated sample and to a method and apparatus for automatically extracting fractions from a fractionated sample and in particular to such a method and apparatus wherein the fractionated sample is a fractionated blood sample.

Blood samples are often analysed or processed by fractionation to separate particular components. This allows particular components of interest to be extracted from a sample. Fractionation is achieved by centrifugation of the sample, which results in a sample having a number of layers or fractions, each fraction consisting of particular components of the blood. Typically, the centrifuged sample comprises three fractions, the uppermost fraction containing (amongst other components) plasma, the lowermost fraction containing (amongst other components) red blood cells and the middle fraction, known as the 'buffy coat', containing (amongst other components) white blood cells.

The fractions are typically extracted in turn by a pipette means under manual control. The fraction containing the component of interest is retained and the other fractions may be retained or disposed of as desired. Manually controlled extraction in this manner is time consuming and expensive. It is also requires considerable skill as, to the naked eye, the boundaries between fractions can be difficult to distinguish. These problems are exacerbated if the 'buffy coat' is the fraction of interest, for instance if DNA analysis of the sample is required, as the buffy coat is typically relatively thin in relation to the other fractions.

It is therefore an object of the present invention to provide a method and apparatus for automating some or all of this process.

SUMMARY OF THE INVENTION

According to a first aspect of the present invention there is provided a method of determining the boundaries between fractions in a fractionated sample, the method comprising the steps of: providing the fractionated sample in a receptacle, the receptacle having at least a transparent window; providing a datum means; positioning the receptacle in a known position relative to the datum means; capturing an image of the receptacle and datum means; and processing the image to determine the position of boundaries between the fractions in the sample relative to the datum means.

This thus provides an automatic method for determining the position of the boundaries between fractions within a sample. Once the boundaries are determined automatically, extraction of fractions of interest can also be carried out automatically.

The image capture may be carried out by a digital imaging means, such as a digital camera.

The digital image is preferably processed using an edge detection algorithm to determine the position of the boundaries between fractions.

If a receptacle of known dimensions is used, the processing may further include the step of calculating the volume of each fraction.

The receptacle may be illuminated by white, coloured or filtered light in order to improve the quality of the captured image or the contrast between fractions. In particular, red light may be used. Additionally or alternatively, the image may be captured through a filter, if desired, to improve the contrast between fractions.

The datum means is preferably a datum plate upon which the receptacle may be positioned. The datum plate may be movable between an operational position and a stowed position. The digital imaging means is preferably mounted in a fixed relation to the operational position of the datum plate.

In use, a receptacle is held at a known orientation and positioned on the datum plate when the datum plate is in the operational position. This allows the position of the lower end of the receptacle to be determined and hence the relative positions of the fraction boundaries in the sample to be determined.

A calibration means may be provided on the datum plate if desired. The calibration means may be provided with suitable markings or formations to allow any or all of the focus, colour, contrast or brightness levels or alignment of the imaging means to be determined and adjusted.

Preferably, the method further comprises the additional step of extracting a selected fraction or fractions of interest from the sample. Extraction is preferably achieved by a pipette means. The pipette means is preferably inserted into a selected fraction and operated so as to aspirate a volume substantially equal to the volume of the selected fraction.

Preferably, the fractions are aspirated in order starting with the uppermost fraction. If the fraction of interest is not the uppermost fraction, then once the uppermost fraction is aspirated it may be discarded and the next fraction then aspirated. Once the fraction of interest is aspirated, it may be dispensed into another receptacle for storage or analysis.

As the fraction boundaries may be intermingled, it may be desirable to extract a volume of material equal to a volume slightly larger or slightly smaller than the fraction providing the maximum amount of the component of interest or the maximum concentration of the component of interest respectively.

The receptacle is preferably a test tube of known dimensions, such as a Falcon™ tube. A processing means is preferably provided for determining the positions of the fraction boundaries and calculating the volume of each fraction. The processing means may additionally control the pipette means.

According to a second aspect of the present invention there is provided a method of extracting a selected fraction of a fractionated sample, the method comprising the following steps: providing the fractionated sample in a receptacle, the receptacle having at least a transparent window; providing a datum means; positioning the receptacle in a known position relative to the datum means; capturing an image of the receptacle and datum means; processing the image to determine the position of boundaries between the fractions in the sample relative to the datum means; calculating the volume of each fraction in the receptacle from the determined positions of the boundaries between the fractions and the dimensions of the receptacle; inserting a pipette means into the selected fraction and operating the pipette means so as to aspirate a volume substantially equal to the calculated volume of the selected fraction.

The second aspect of the invention may incorporate any or all of the features described in relation to the first aspect of the present invention as appropriate or as desired.

According to a third aspect of the present invention there is provided an apparatus suitable for determining the boundaries between fractions in a fractionated sample, the apparatus comprising: a receptacle for holding a fractionated sample, the receptacle having at least a transparent window; a datum means; positioning means for positioning the receptacle in a known position relative to the datum means; imaging means for capturing a image of the receptacle and datum means; and processing means for processing the image to determine the position of the fraction boundaries relative to the datum means.

According to a fourth aspect of the present invention there is provided an apparatus suitable for extracting a selected fraction of a fractionated sample, the apparatus comprising: a receptacle for holding a fractionated sample, the receptacle having at least a transparent window; a datum means; positioning means for positioning the receptacle in a known position relative to the datum means; imaging means for capturing a image of the receptacle and datum means; and processing means for processing the image to determine the position of the fraction boundaries relative to the datum means and for calculating the volume of each fraction of a fractionated sample from the determined positions of the boundaries between the fractions and the dimensions of the receptacle.

The apparatus according to the third or fourth aspects of the invention may incorporate means relating to any or all of the features described in relation to the methods of the first aspect or second aspects of the present invention as appropriate or as desired.

The apparatus may include automated robotic apparatus to achieve full automation of the process.

Preferably the above method and apparatus is adapted for determining the boundaries between fractions in a fractionated sample and extracting desired fractions from the fractionated sample in the case wherein the sample is a fractionated blood sample. In particular this method and apparatus may be applied to extracting the buffy coat fraction from a fractionated blood sample. It is of course possible to apply this technique to the determination of boundaries between fractions and the extraction of fractions in other types of fractionated sample.

The skilled man will of course appreciate that the above method and apparatus may be adapted to allow a plurality of samples to be processed at any one time.

BRIEF DESCRIPTION OF THE DRAWINGS

In order that the invention is more clearly understood, one embodiment will now be described in greater detail below, with reference to the accompanying drawings, in which.

DETAILED DESCRIPTION OF THE PREFERRED EMBODIMENTS

Figure 1:
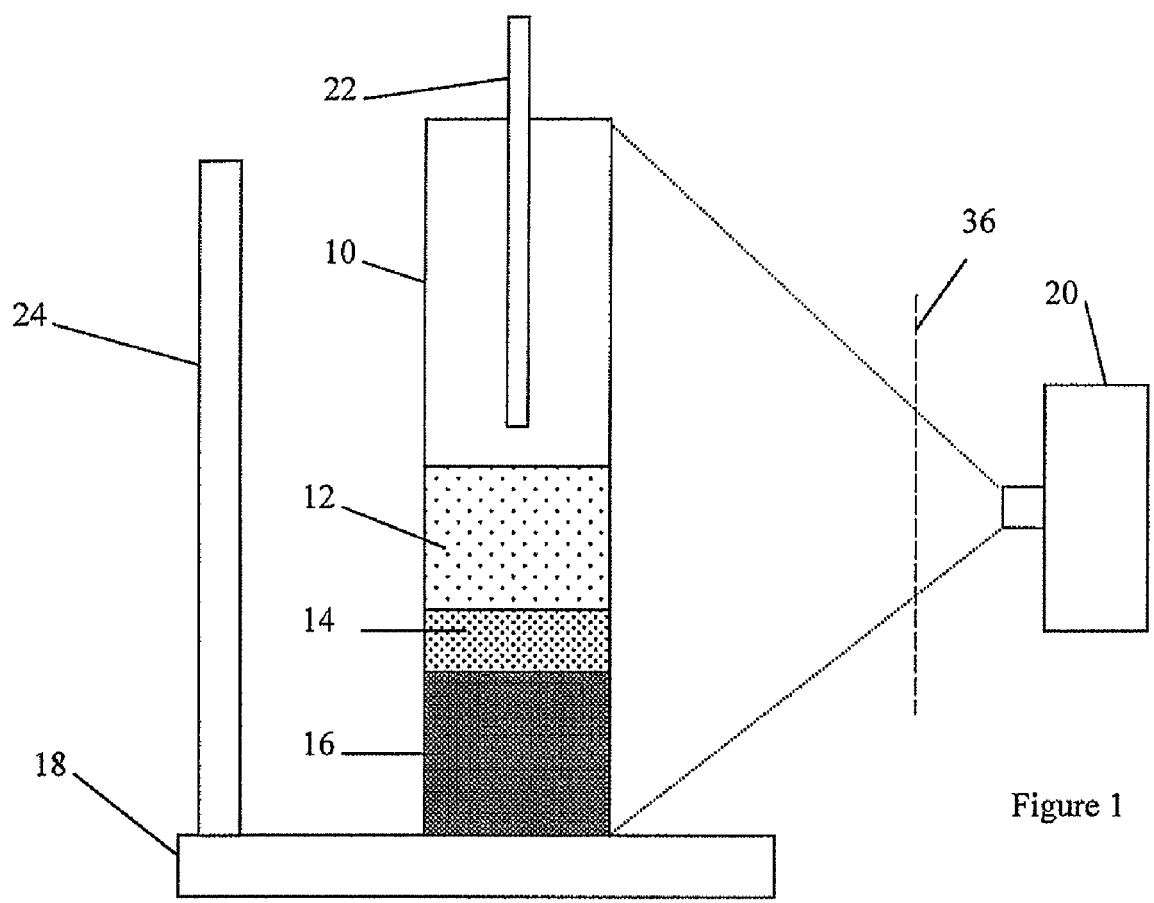
FIG. 1 is a schematic diagram showing a fractionated blood sample in a test tube and features of an apparatus for identifying and extracting desired fractions of the sample.

Referring now to FIG. 1, a fractionated blood sample is provided in a test tube 10. The sample has three fractions, an uppermost or 'plasma' fraction 12, a lowermost or 'red blood cell' fraction 16 and an intermediate or 'buffy coat' fraction 14, which contains white blood cells.

The test tube 10 of this embodiment is entirely transparent such that the entire test tube acts as a viewing window. As an alternative, the test tube 10 could have a portion of the tube acting as a viewing window. The window need not be 100% transparent but may be partially transparent.

In order to determine the position of the fraction boundaries, the test tube 10 is held vertically and positioned with its lower end in contact with a datum plate 18. An image of the test tube 10 is then captured by digital camera 20. The image is then processed by a suitable processing means 100 to determine the positions of the fraction boundaries relative to the datum plate 18. The processing means 100 typically achieves this by use of edge detection algorithms.

In order that a better quality image can be captured the test tube 10 may be illuminated by white, coloured or filtered light as required. A calibration means 24 may be provided adjacent to the test tube 10. The calibration means 24 may be provided with suitable markings to allow the focus, colour, brightness or contrast levels or alignment of camera 20 to be adjusted. A filter 36 may be provided to improve the contrast between fractions in the sample.

The test tube 10 is of known dimensions. Thus from the determined position of each fraction boundary, the volume of each fraction can be calculated by the processing means 100. The processing means may then control an automatic pipette means 22. The pipette means can be inserted into the sample to a desired position and used to aspirate a volume equal to the calculated volume of a particular fraction. Typically, the fractions are aspirated in turn starting with the uppermost. Those fractions which are not of particular interest may be discarded after aspiration and those fractions which are of further interest may be dispensed into other receptacles for storage or analysis.

As an example, if it is desired to extract the buffy coat 14 for further analysis, the pipette means is used to aspirate the plasma fraction 12 to a level just above the upper boundary of the buffy coat 14. The aspirated plasma fraction 12 is then discarded. The pipette means is then used to aspirate the buffy coat 14 to a level just below the lower boundary of the buffy coat 14. The buffy coat 14 material in the pipette means 22 may then be transferred to a further receptacle for storage or analysis.

It is of course possible that if a more concentrated sample of buffy coat fraction 14 is required, the plasma fraction 12 can be aspirated to a level just below the upper boundary of the buffy coat 14 and subsequently, the buffy coat fraction 14 can be aspirated to a level just above the lower boundary of the buffy coat 14. In a further alternative, it is possible that the buffy coat fraction 14 may be extracted in a single operation by positioning the tip of the pipette means 22 either just above or just below the lower boundary of the buffy coat fraction 14 as desired and aspirating a volume of material equal to the volume of the buffy coat fraction 14.

Figure 2:
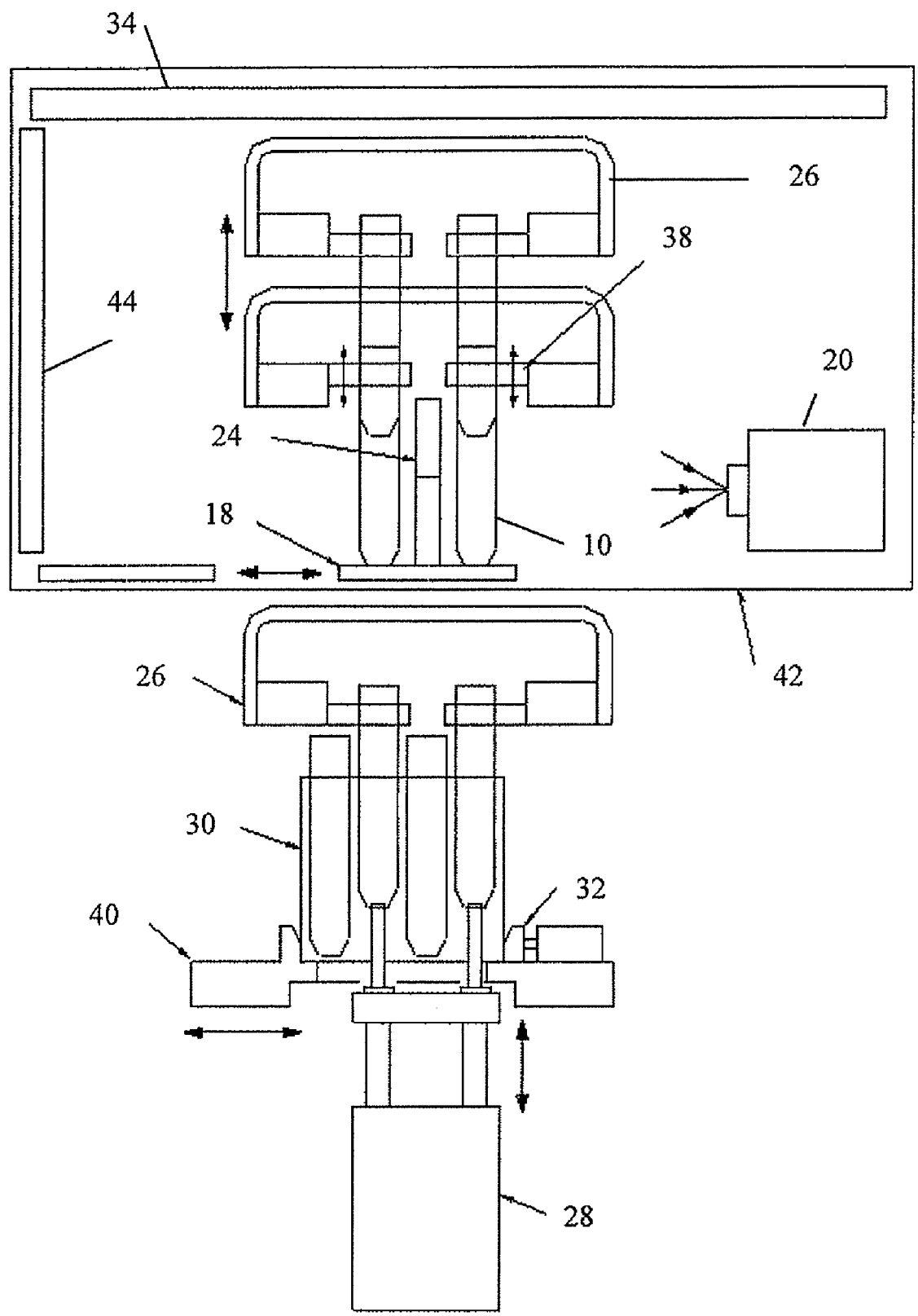
FIG. 2 is a schematic diagram of features of an apparatus for identifying and extracting desired fractions from a plurality of samples.

FIG. 2 illustrates schematically how this method and apparatus may be applied to process a plurality of fractionated samples. In FIG. 2, a plurality of samples are each retained in test tubes 10. The test tubes 10 are held in a tube rack 30. The tube rack 30 may optionally be provided with releasable rack clamps 32 to further secure the test tubes 30.

Back light 44 illuminates an optical booth 42 with white, coloured or filtered light as required. Back light 44 is used generally to illuminate the top level of the samples and the orientation of the test tubes 10. Light 34 is provided above the samples and is used to identify the buffy coat fraction 14.

A tube pop-up actuator 28 may be used to raise one or more tubes 10 into a position whereby the tube can be gripped by tube gripping means 26. This is facilitated by utilization of an X-Y table 40 enabling the plurality of tubes to be positioned suitably corresponding to the actuator 28. The tube gripping means has gripper jaws 38 ensuring vertical compliance of the tubes 10. The tube gripping means 26 is then operable to position the tubes 10 on the datum plate 18. The gripper jaws 38 enable the tubes 10 to be held securely until reaching the datum plate 18 at which point they are able to rest on the datum plate 18. The datum plate 18 may itself be movable from a stowed position to an operational position to facilitate the movement of the tubes 10 by the tube gripping means 26 into position on the datum means 18. After the fraction boundaries are determined and any desired fractions are extracted, the tube gripping means 26 is operable to either return the tubes 10 to their original rack 30 or to place the tubes 10 in a different tube rack 30. The tube gripping means 26 is moved between the required positions by an actuator (not shown).

In the case wherein more than one tube 10 is selected from the rack, the tubes 10 may be imaged and have their fractions extracted simultaneously or in turn. If the imaging is to be carried out simultaneously either individual cameras 20 may be provided for each tube or alternatively one camera may be provided for imaging a plurality of tubes. Additionally, if fractions in a plurality of tubes 10 are to be extracted simultaneously the pipette means 22 is provided with a plurality of pipette heads, each pipette head being individually controllable. This allows the pipette heads to extract the correct amount of material from each test tube 10.

Figure 3:
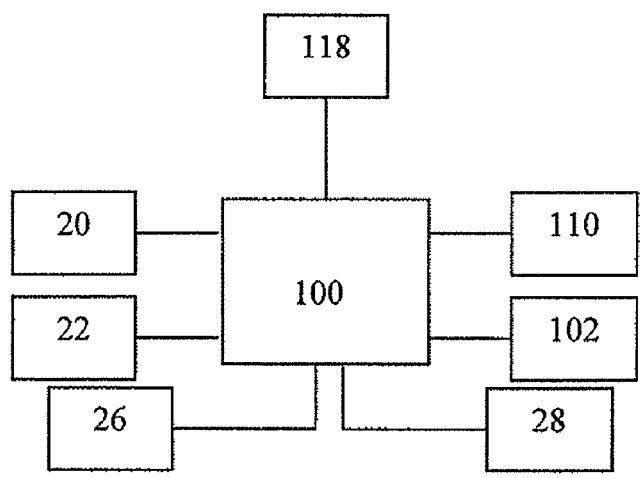
FIG. 3 is a schematic block diagram of the control circuitry for such an apparatus.

FIG. 3 shows how the various components of the apparatus may be connected. The processing means 100 is connected directly to the camera 20, the pipette means 22, the tube gripping means 26, the pop-up actuators 28 and to datum plate moving means 118. The processing means may also be provided with a user interface 102. The processing means may also be connected to means 110 for controlling the illumination of the tubes 10 during image capture. In one preferred embodiment, the processing means and user interface may be provided by a computer or computer system.

It is of course to be understood that the invention is not to be limited to the details of the above embodiment, which is described by way of example only. Many variations are possible within the scope of the following claims.

What is claimed is:

1. A method of determining boundaries between fractions in a fractionated sample, the method comprising the steps of:
    providing the fractionated sample in a receptacle, the receptacle having at least a transparent window;
    providing a datum means;
    positioning the receptacle in a known position relative to the datum means;
    illuminating the receptacle substantially from a side thereof, to illuminate the top level of the sample;
    illuminating the receptacle substantially from above to identify a fraction within the sample;
    capturing an image of the receptacle and datum means; and
    processing the image to determine the position of boundaries between the fractions in the sample relative to the datum means.

2. The method of claim 1, wherein the step of capturing an image includes using a digital imaging means.

3. The method of claim 2, wherein the step of processing the image includes using an edge detection algorithm to determine the position of the boundaries between the fractions.

4. The method of claim 3, wherein the step of processing the image further comprises a step of calculating the volume of each fraction.

5. The method of claim 2, wherein the datum means is a datum plate upon which the receptacle is positioned and the datum plate is moveable between an operational position and a stowed position and the digital imaging means is mounted in a fixed relation to the operational position of the datum plate.

6. The method of claim 1, wherein the receptacle is illuminated by white, coloured or filtered light, thereby to improve the quality of the captured image or the contrast between fractions.

7. The method of claim 1, wherein the step of capturing an image includes capturing the image through a filter thereby to improve the contrast between fractions.

8. The method of claim 1, wherein the datum means is a datum plate upon which the receptacle is positioned and the datum plate is moveable between an operational position and a stowed position.

9. The method of claim 8, wherein the step of positioning the receptacle includes holding the receptacle at a known orientation and position on the datum plate while the datum plate is in the operational position thereby enabling the position of the lower end of the receptacle to be determined and the relative positions of the fraction boundaries in the sample to be determined.

10. The method of claim 8, further comprising a step of providing a calibration means on the datum plate.

11. The method of claim 10, wherein the calibration means has markings or formations to allow any or all of the focus, colour, contrast or brightness levels or alignment of the imaging means to be determined and adjusted.

12. The method of claim 1, further comprising a step of extracting a selected fraction or fractions of interest from the sample.

13. The method of claim 12, wherein the step of extraction is achieved by using pipette means and the pipette means is inserted into a selected fraction and operated so as to aspirate a volume substantially equal to the volume of the selected fraction.

14. The method of claim 13, wherein the fractions are aspirated in order starting with the uppermost fraction and the fractions are aspirated and then discarded until a fraction of interest is aspirated, which is dispensed into another receptacle.

15. The method of claim 13, wherein the step of processing the image further comprises providing a processing means to determine the positions of the fraction boundaries and calculating the volume of each fraction, and controlling the pipette means using the processing means.

16. The method of claim 1, wherein the two illumination steps are performed separately.

17. The method of claim 1, wherein the step of illuminating the receptacle substantially from a side thereof is performed using a first source of illumination positioned alongside the receptacle and the step of illuminating the receptacle from above is performed using a second source of illumination positioned above the receptacle.

18. The method of claim 1 wherein the fractionated sample is a fractionated blood sample and the receptacle is illuminated from above to identify a buffy coat fraction in the sample.

19. A method of extracting a selected fraction of a fractionated sample, comprising:
    providing the fractionated sample in a receptacle, the receptacle having at least a transparent window;
    providing a datum means;

positioning the receptacle in a known position relative to the datum means;

illuminating the receptacle substantially from a side thereof, to illuminate the top level of the sample;

illuminating the receptacle substantially from above to identify a fraction within the sample;

capturing an image of the receptacle and datum means;

processing the image to determine the position of the boundaries between the fractions in the sample relative to the datum means;

calculating the volume of each fraction in the receptacle from the determined positions of the boundaries between the fractions and the dimensions of the receptacle; and inserting a pipette means into the selected fraction and operating the pipette means so as to aspirate a volume substantially equal to the calculated volume of the selected fraction.

20. An apparatus for determining the boundaries between fractions in a fractionated sample, comprising:

a receptacle for holding a fractionated sample, the receptacle having at least a transparent window;

a datum means;

positioning means for positioning the receptacle in a known position relative to the datum means;

a source of illumination arranged to illuminate the receptacle substantially from a side thereof;

a source of illumination arranged to illuminate the receptacle substantially from above;

imaging means for capturing images of the receptacle and datum means; and processing means for processing the images to determine the position of the fraction boundaries relative to the datum means.

21. The apparatus of claim 20, wherein the imaging means is a digital imaging means.

22. The apparatus of claim 20, wherein the processing means uses an edge detection algorithm to determine the position of the fraction boundaries in a fractionated sample.

23. The apparatus of claim 20, wherein the processing means is operative to calculate the volume of each fraction in a fractionated sample.

24. The apparatus of claim 20, wherein each source of illumination is a source of white, coloured or filtered light.

25. The apparatus of claim 20, further comprising a filter provided between the receptacle and the imaging means to improve contrast between fractions in a fractionated sample.

26. The apparatus of claim 20, wherein the datum means is a datum plate.

27. The apparatus of claim 26, wherein a calibration means is provided on the datum plate.

28. The apparatus of claim 27, wherein the calibration means has markings or formations to allow any or all of the focus, colour, contrast or brightness levels or alignment of the imaging means to be determined and adjusted.

29. The apparatus of claim 20, further comprising pipette means operative to aspirate a chosen volume of the selected fraction.

30. The apparatus of claim 29, wherein the pipette means is operative to aspirate a volume substantially equal to the calculated volume of the selected fraction.

31. The apparatus of claim 29, wherein the processing means is operative to control the pipette means.

32. The apparatus of claim 20, wherein the apparatus includes automated robotic apparatus.

33. Use of the apparatus of claim 20 in determining the boundaries between fractions in a fractionated sample.

34. The apparatus of claim 33, further comprising pipette means operative to aspirate a chosen volume of the selected fraction.

35. The apparatus of claim 33, wherein the apparatus includes automated robotic apparatus.

36. Use of the apparatus of claim 33 in extracting a selected fraction of a fractionated sample.

37. The apparatus of claim 20 wherein the source of illumination arranged to illuminate the receptacle substantially from a side thereof is a first light, positioned alongside the receptacle and the source of illumination arranged to illuminate the receptacle substantially from above is a second light, positioned above the receptacle.

38. An apparatus for extracting a selected fraction of a fractionated sample, comprising:

a receptacle for holding a fractionated sample, the receptacle having a transparent window;

a datum means;

positioning means for positioning the receptacle in a known position relative to the datum means;

a source of illumination arranged to illuminate the receptacle substantially from a side thereof;

a source of illumination arranged to illuminate the receptacle substantially from above;

imaging means for capturing an image of the receptacle and datum means; and processing means for processing the image to determine the position of the fraction boundaries relative to the datum means and for calculating the volume of each fraction of a fractionated sample from the determined positions of the boundaries between the fractions and the dimensions of the receptacle.

39. The apparatus of claim 38, wherein the pipette means is operative to aspirate a volume substantially equal to the calculated volume of the selected fraction.

40. The apparatus of claim 38, wherein the processing means is operative to control the pipette means.

* * * * *